United States Patent
Oikawa

(10) Patent No.: US 10,005,035 B2
(45) Date of Patent: Jun. 26, 2018

(54) ION PROCESSING DEVICE, ION CHROMATOGRAPH PROVIDED WITH THE ION PROCESSING DEVICE, AND ELUENT GENERATOR PROVIDED WITH THE ION PROCESSING DEVICE

(71) Applicant: SHIMADZU CORPORATION, Kyoto-shi, Kyoto (JP)

(72) Inventor: Yukio Oikawa, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 233 days.

(21) Appl. No.: 14/962,106

(22) Filed: Dec. 8, 2015

(65) Prior Publication Data
US 2016/0175778 A1 Jun. 23, 2016

(30) Foreign Application Priority Data
Dec. 19, 2014 (JP) ................... 2014-257774

(51) Int. Cl.
*A01B 1/00* (2006.01)
*G01N 30/96* (2006.01)
(Continued)

(52) U.S. Cl.
CPC ......... *B01D 61/445* (2013.01); *B01D 15/24* (2013.01); *B01D 15/361* (2013.01);
(Continued)

(58) Field of Classification Search
CPC ...... G01N 30/02; G01N 30/32; G01N 30/461; G01N 30/74; G01N 30/24; G01N 30/34;
(Continued)

(56) References Cited

U.S. PATENT DOCUMENTS 3,926,559 A * 12/1975 Stevens ............... G01N 30/461
                                                      210/284
5,518,622 A *  5/1996 Stillian ................. G01N 30/96
                                                      204/542
(Continued)

FOREIGN PATENT DOCUMENTS

JP           9-236589 A      9/1997

OTHER PUBLICATIONS

Office Action dated Feb. 20, 2018, issued in counterpart Japanese Application No. 2014-257774, with English machine translation. (6 pages).

*Primary Examiner* — John Fitzgerald
*Assistant Examiner* — Truong D Phan
(74) *Attorney, Agent, or Firm* — Westerman, Hattori, Daniels & Adrian, LLP

(57) ABSTRACT

An ion processing device includes, on the side of an anion exchange layer of a bipolar membrane which is formed by stacking an anion exchange layer and a cation exchange layer, an anion-side channel which is filled with an anion exchanger, and an anion removal channel provided via an anion exchange membrane, and also includes an anode for moving anions from the anion-side channel to the anion removal channel through the anion exchange membrane. Further, a cation-side channel which is filled with a cation exchanger and a cation removal channel provided via a cation exchange membrane are included on the side of the cation exchange layer of the bipolar membrane as well as a cathode for moving cations from the cation-side channel to the cation removal channel through the cation exchange membrane.

3 Claims, 3 Drawing Sheets

(51) Int. Cl.
  *B01D 61/48* (2006.01)
  *B01D 15/42* (2006.01)
  *B01D 15/24* (2006.01)
  *B01D 15/36* (2006.01)
  *B01D 61/44* (2006.01)

(52) U.S. Cl.
  CPC ......... *B01D 15/424* (2013.01); *B01D 61/485* (2013.01); *G01N 30/96* (2013.01); *G01N 2030/965* (2013.01)

(58) Field of Classification Search
  CPC ........ G01N 1/2035; G01N 1/40; G01N 30/56; G01N 31/16; G01N 31/166; G01N 30/96; G01N 27/06; G01N 31/12; G01N 33/1846; G01N 31/005; G01N 2030/025; G01N 30/30; G01N 30/12; G01N 27/12; G01N 27/126; G01N 27/4162; G01N 2030/965; B01D 15/08; B01D 61/145; B01D 61/142; B01D 61/025; B01D 61/40; B01D 61/38; B01D 61/18; B01D 15/00; B01D 61/445; B01D 61/485; B01D 15/24; B01D 15/361; B01D 15/424; B01D 61/44; B01D 53/501; B01D 53/60; B01D 69/141; B01J 2220/54; B01J 20/32; B01J 39/185; B01L 3/502715; C02F 9/00; C02F 1/441; C02F 1/42; C02F 1/26; C02F 1/444; C02F 1/281; C02F 1/283; C02F 2101/103; C23G 1/36; C08J 5/2275; C08J 5/2287; C25B 1/46
  USPC .......... 73/61.52–61.55, 64.56; 210/635, 638, 210/641, 643, 650, 656, 660, 681, 683, 210/198.2; 436/161; 204/534, 537–538, 204/631, 533, 633, 520, 536, 522, 630, 204/252, 230.2, 229.4; 205/344, 749, 205/742; 422/89, 80, 90, 70, 76
  See application file for complete search history.

(56) References Cited

U.S. PATENT DOCUMENTS

| | | | |
|---|---|---|---|
| 5,788,828 A * | 8/1998 | Nakatsu | G01M 3/16 204/632 |
| 6,077,434 A | 6/2000 | Srinivasan et al. | |
| 7,892,848 B2 * | 2/2011 | Riviello | B01D 61/48 210/198.2 |
| 2003/0001090 A1* | 1/2003 | Ranasinghe | H01J 49/40 250/288 |
| 2003/0127392 A1* | 7/2003 | Srinivasan | B01D 61/44 210/656 |
| 2008/0314129 A1* | 12/2008 | Schultz | G01N 30/80 73/61.55 |
| 2010/0108521 A1* | 5/2010 | Riviello | B01D 61/48 204/632 |
| 2010/0320132 A1* | 12/2010 | Sakamoto | B01D 61/44 210/198.2 |
| 2013/0220814 A1* | 8/2013 | Dasgupta | B01D 61/44 204/533 |
| 2014/0251824 A1* | 9/2014 | Astle | B01J 47/08 205/749 |
| 2014/0332387 A1* | 11/2014 | Srinivasan | G01N 30/56 204/536 |
| 2016/0145125 A1* | 5/2016 | Riviello | C02F 1/4695 204/632 |

* cited by examiner

ION PROCESSING DEVICE, ION CHROMATOGRAPH PROVIDED WITH THE ION PROCESSING DEVICE, AND ELUENT GENERATOR PROVIDED WITH THE ION PROCESSING DEVICE

BACKGROUND OF THE INVENTION

1. Field of the Invention

The present invention relates to an ion processing device, an ion chromatograph provided with the ion processing device as a suppressor, and an eluent generator provided with the ion processing device.

2. Description of the Related Art

An ion chromatograph detects component ions by introducing a sample into a separation column, separating the sample into component ions, and then guiding the eluent from the separation column into a cell of a conductivity detector and detecting the conductivity. At this time, a suppressor is arranged between the separation column and the conductivity detector so that the conductivity of the eluent from the separation column is reduced by unnecessary ions being removed from the eluent so as to allow highly sensitive measurement. An electrodialysis suppressor may be cited as such a suppressor.

An ion chromatograph provided with an electrodialysis suppressor is described in, for example, U.S. Pat. No. 6,077,433. As shown in FIG. 3, according to a conventional ion chromatograph provided with an electrodialysis suppressor 101, an eluent is delivered from an eluent reservoir 103 by a pump 105, and a sample is injected by a sample injection valve 107 and is separated by a separation column 109.

A separated sample is introduced into an ion exchange membrane device 113 by a conduit 111, and is detected by a conductivity detector 117 through the conduit 115. A detector effluent from the conductivity detector 117 passes through a splitter valve 119 formed from a three-way valve. The splitter valve 119 divides the detector effluent into two different conduits 121 and 123, and supplies the detector effluent to through channels on the opposite sides of two respective membranes adjacent to a center sample flow channel inside the ion exchange membrane device 113. The detector effluents which have passed through the through channels are disposed through a conduit 125.

According to conventional technology, after an anion sample or a cation sample separated by the separation column has passed through its dedicated suppressor, one of the ions desired to be detected is detected by the conductivity detector. Furthermore, according to conventional technology, the anions or the cations are separately measured in a suppressor operation mode and a non-suppressor operation mode.

An eluent generator is used to adjust an eluent to be used by an ion chromatograph to an optimal concentration. Conventionally, an eluent generator for an eluent for anion analysis and an eluent generator for an eluent for cation analysis each having individual functions are configured.

SUMMARY OF THE INVENTION

According to conventional technology, an eluent stream containing a sample is deionized by electrodialysis via an ion exchange membrane, and the remaining ions of the opposite charge are detected by conductivity detector. Moreover, conventional technology uses liquid waste as electrode water for a regenerator. In this case, sample analysis for only anions or cations is possible with one suppressor. Accordingly, with conventional technology, it is difficult to suppress the background of an eluent and to measure by one device both anions and cations which are analysis targets.

The first object of the present invention is to provide an ion processing device which is capable of processing both anions and cations of an eluent by one device.

The second object of the present invention is to provide an ion chromatograph which uses the ion processing device as a suppressor which is capable of suppressing the background of anions and cations.

The third object of the present invention is to provide an eluent generator which is capable of generating an electrolyte solution which has been adjusted to a desirable ion concentration by the ion processing device of the present invention.

The ion processing device of the present invention includes a bipolar membrane that is formed by stacking an anion exchange layer and a cation exchange layer, an anion-side channel that is arranged in contact with the anion exchange layer of the bipolar membrane, and that is filled with an anion exchanger, an anion removal channel that is arranged in contact with the anion-side channel via an anion exchange membrane, an anode for moving anions from the anion-side channel to the anion removal channel through the anion exchange membrane, a cation-side channel that is arranged in contact with the cation exchange layer of the bipolar membrane, and that is filled with a cation exchanger, a cation removal channel that is arranged in contact with the cation-side channel via a cation exchange membrane, and a cathode for moving cations from the cation-side channel to the cation removal channel through the cation exchange membrane.

The ion chromatograph according to the present invention includes a separation column for separating a sample, an eluent delivery section for delivering an eluent to the separation column, a sample injection section for injecting a sample into a flow of the eluent that is delivered by the eluent delivery section to the separation column, and a suppressor that is connected to an eluent outlet side of the separation column. As the suppressor, the ion processing device described above and a channel branching section for dividing and introducing the eluent flowing out of the separation column into the anion-side channel and the cation-side channel are included. Furthermore, to detect a sample component separated by the separation column, a first conductivity detector that is, with respect to the suppressor, connected to the anion-side channel on an opposite side from the channel branching section, and a second conductivity detector that is, with respect to the ion processing device, connected to the cation-side channel on the opposite side from the channel branching section are provided.

The eluent generator according to the present invention includes the ion processing device described above, a solution supply section, on one side of the ion processing device, for supplying pure water and an electrolyte solution containing cations to the anion-side channel and the cation-side channel, respectively, or for supplying an electrolyte solution containing anions and pure water to the anion-side channel and the cation-side channel, respectively, and a merging section, on another side of the ion processing device, for merging liquids flowing out of the anion-side channel and the cation-side channel.

Specifically, the solution supply section supplies the pure water to the anion-side channel when supplying the electrolyte solution containing cations to the cation-side channel, and supplies the pure water to the cation-side channel when supplying the electrolyte solution containing anions to the anion-side channel.

The ion chromatograph including the ion processing device of the present invention may suppress the background of anions and cations of an eluent by using one ion processing device as a suppressor.

The eluent generator of the present invention may generate an electrolyte solution which has been adjusted to a desirable ion concentration by using the ion processing device of the present invention.

DETAILED DESCRIPTION OF THE INVENTION

Figure 1:
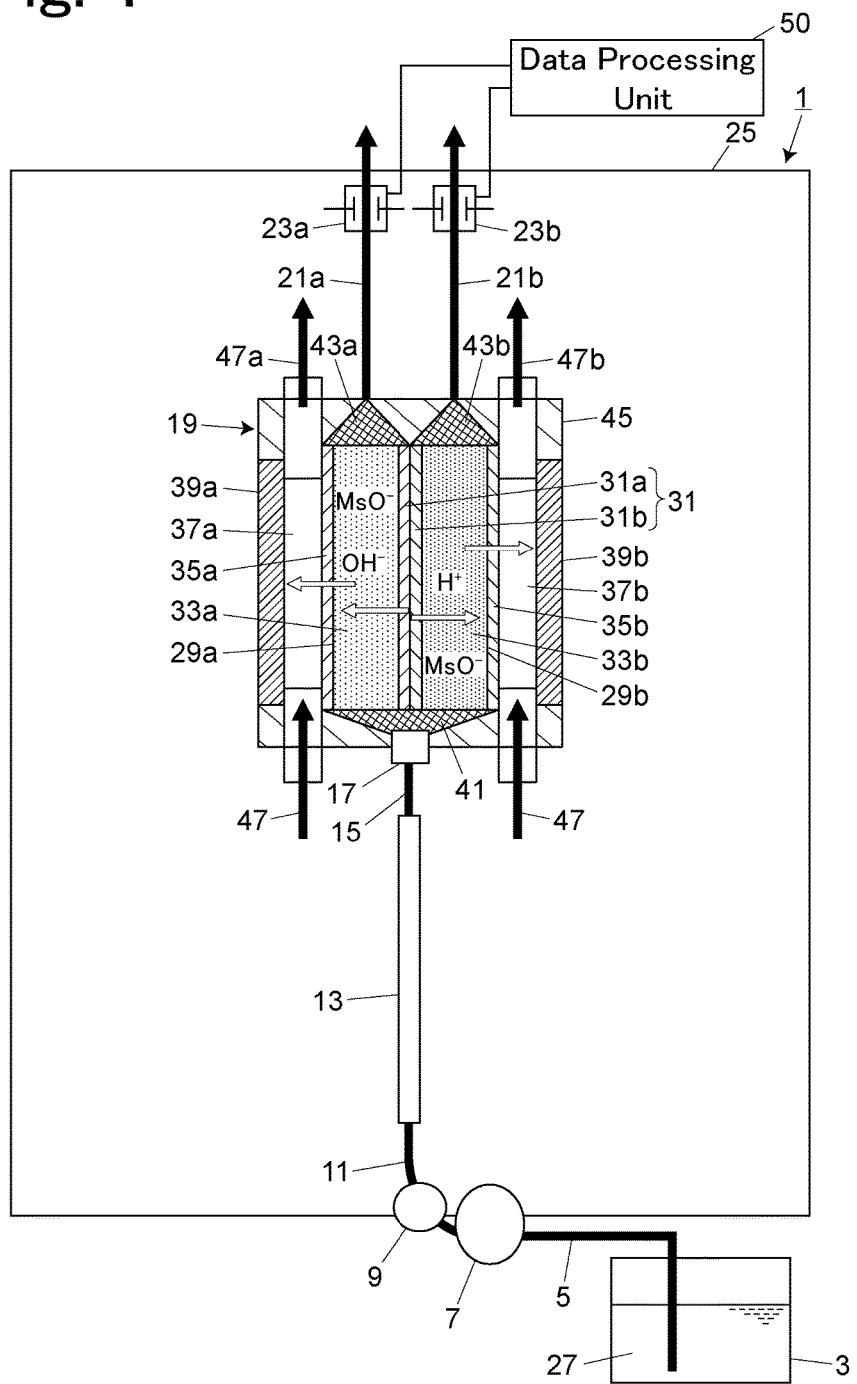
FIG. 1 is a schematic configuration diagram for describing an example of an ion processing device and an ion chromatograph.

An ion processing device according to an embodiment of the present invention may, for example, further include a channel branching section for branching, and introducing liquids to be introduced into the anion-side channel and the cation-side channel into the anion-side channel and the cation-side channel. This eliminates the need to separately prepare a branching unit for branching a liquid which has passed through a separation column, at the time of embedding the ion processing device in an ion chromatograph. However, the ion processing device of the present invention does not have to include the channel branching section. The anion-side channel and the cation-side channel of the ion processing device may be connected to a separation column via a branching unit that is separately prepared.

An ion chromatograph according to an embodiment of the present invention may, for example, simultaneously detect anions or cations by both a non-suppressor method and a suppressor method based on detection signals of both the first conductivity detector and the second conductivity detector. However, the ion chromatograph of the present invention may alternatively detect the anions or the cations by one of the non-suppressor method and the suppressor method.

According to conventional technology, analysis of ion components is performed in the order of (1) a stream including an ion sample, (2) separation at a separation column, (3) removal of ions by a suppressor, and (4) detection (circulation of liquid waste).

An example of an analysis flow where the ion processing device according to an embodiment of the present invention is used is briefly described.

Separation of anions or cations, which are the analysis target, is performed in the process corresponding to (2) mentioned above. Then, in the process corresponding to (3) mentioned above, a stream which has passed through a separation column is divided into two.

The stream which has passed through the separation column is introduced into two chambers (an anion-side channel and a cation-side channel) separated by a bipolar membrane. The chamber is filled with, for example, an anion exchange resin or a cation exchange resin in a bead form. One chamber is filled with the anion exchange resin, and the other chamber is filled with the cation exchange resin.

Of the ions included in the stream which have passed through the separation column, ions of the same charge as the ion exchange resin (for example, anions for the anion exchange resin) are trapped. The trapped ions are moved to outside the chamber via an anion exchange membrane or a cation exchange membrane by electrodialysis and are removed. The streams which have passed through the two chambers are lead to conductivity detectors as two streams.

In the process corresponding to (4) mentioned above, ions are detected for one or both of the two streams which have passed through the chambers.

Moreover, the ion processing device according to an embodiment of the present invention further includes a function for adjusting the eluent used by the ion chromatograph to an optimal concentration.

A chromatograph according to an embodiment of the present invention includes, for example, the ion processing device of the present invention including a bipolar membrane, an anion-side channel, a cation-side channel, an anion exchanger, a cation exchanger, an anion exchange membrane, a cation exchange membrane, an anion removal channel, a cation removal channel, an anode and a cathode, an eluent, pure water, an eluent reservoir, a separation column for anion analysis or cation analysis, a conductivity detector, and conduits for connecting the same.

An ion chromatograph having a conventional electrodialysis suppressor detects, by a conductivity detector, the ions of one of an anion sample and a cation sample separated by a separation column desired to be detected, after causing the anion sample or the cation sample to pass through an independent suppressor for anions or cations. Further, there has been no independent device that simultaneously performs analysis by a non-suppressor method and a suppressor method by one measurement.

According to an embodiment of the present invention, first, analysis target anions and analysis target cations which have been separated by the separation column are introduced, respectively, into the anion-side channel and the cation-side channel divided by the bipolar membrane. Ions in the eluents of the same charges as the ion exchangers accommodated in the channels are trapped. The trapped anions or cations are electrically moved and removed through the ion exchange membrane. With respect to the anions or the cations as the analysis target, one channel is on the pure water side (the suppressor method) and the other channel is on the eluent side (the non-suppressor method). The analysis target ions flow out from two channel outlets of the ion processing device. The ions are detected on both the pure water side and the eluent side, and thus, the analysis target ions may be detected by both the non-suppressor method and the suppressor method.

According to an embodiment of the present invention, the anion exchanger and the cation exchanger are arranged being divided by the bipolar membrane, and analysis of the anions and the cations may be performed by one suppressor (the ion processing device). Moreover, according to the present invention, analysis by the non-suppressor method and the suppressor method may be performed by one suppressor.

Furthermore, according to an embodiment of the present invention, analysis by the non-suppressor method and the suppressor method may be performed in parallel by one suppressor. Accordingly, data by the suppressor method and the non-suppressor method may be swiftly compared, and the analysis time may be reduced, and moreover, the running cost is thought to be further reduced by multi-functionalization.

FIG. 1 is a schematic configuration diagram for describing an example of the ion processing device and the ion chromatograph.

An ion chromatograph 1 roughly includes an eluent reservoir 3, a conduit 5, a pump 7, a sample injection section 9, a conduit 11, a separation column 13, a conduit 15, a connector 17, an ion processing device 19, conduits 21a and 21b, a first conductivity detector 23a, a second conductivity detector 23b, and an oven 25.

The eluent reservoir 3 is for containing an eluent 27. The eluent 27 is, for example, 2.5 mM methanesulfonic acid. The pump 7 is for delivering the eluent 27. The eluent reservoir 3 and the pump 7 are connected by the conduit 5. The eluent reservoir 3 containing the eluent 27 and the pump 7 constitute the eluent delivery section.

The sample injection section 9 is for injecting a sample into the flow of the eluent 27. The sample injection section 9 is provided along the conduit 11 connecting the pump 7 and the separation column 13. The separation column 13 is for separating the sample injected by the sample injection section 9. The separation column 13 is, for example, IC-C4: 4.6 mm I.D.×150 mm (a column for cation analysis) of Shimadzu Corporation. The ion processing device 19 includes an anion-side channel 29a, and a cation-side channel 29b. Details of the ion processing device 19 will be given later.

The conduit 15 and the connector 17 are for connecting the separation column 13 with the anion-side channel 29a and the cation-side channel 29b of the ion processing device 19.

The conduit 21a is connected to the anion-side channel 29a of the ion processing device 19. The first conductivity detector 23a is connected to the anion-side channel 29a via the conduit 21a.

The conduit 21b is connected to the cation-side channel 29b of the ion processing device 19. The second conductivity detector 23b is connected to the cation-side channel 29b via the conduit 21b.

The conduit 11, the separation column 13, the conduit 15, the connector 17, the ion processing device 19, the conduits 21a and 21b, and the first conductivity detector 23a and the second conductivity detector 23b are arranged inside the oven 25.

A detection signal of the first conductivity detector 23a and a detection signal of the second conductivity detector 23b are input to a data processing unit 50, and are processed. The data processing unit 50 is configured, for example, to detect, based on the detection signals, the anions or the cations simultaneously by both the non-suppressor method and the suppressor method. The data processing unit 50 is realized by a computer dedicated to the ion chromatograph or by a general-purpose personal computer.

The ion processing device 19 will be described. The ion processing device 19 includes the anion-side channel 29a, a bipolar membrane 31, an anion exchanger 33a, an anion exchange membrane 35a, an anion removal channel 37a, an anode 39a, the cation-side channel 29b, a cation exchanger 33b, a cation exchange membrane 35b, a cation removal channel 37b, a cathode 39b, a channel branching section 41, frits 43a and 43b, and a container 45 for accommodating the above.

The bipolar membrane 31 is formed by stacking an anion exchange layer 31a and a cation exchange layer 31b. A bipolar membrane 31 produced by, for example, ASTOM Corporation may be used.

The anion-side channel 29a is arranged in contact with the anion exchange layer 31a of the bipolar membrane 31. The anion exchanger 33a is accommodated inside the anion-side channel 29a. The anion exchanger 33a is, for example, an anion exchange resin. The anion exchange resin may be a commercially available product, and may be, for example, IRA410J produced by Organo Corporation The anion exchange membrane 35a is arranged in such a way as to contact a liquid that is introduced into the anion-side channel 29a. The anion removal channel 37a is arranged on the opposite side of the anion exchange membrane 35a from the anion-side channel 29a. The anode 39a is for moving anions from the anion-side channel 29a to the anion removal channel 37a through the anion exchange membrane 35a.

The cation-side channel 29b is arranged in contact with the cation exchange layer 31b of the bipolar membrane 31. The cation exchanger 33b is accommodated inside the cation-side channel 29b. The cation exchanger 33b is, for example, a cation exchange resin. The cation exchange resin may be a commercially available product, and may be, for example, IR120B produced by Organo Corporation.

The cation exchange membrane 35b is arranged in such a way as to contact a liquid that is introduced into the cation-side channel 29b. The cation removal channel 37b is arranged on the opposite side of the cation exchange membrane 35b from the cation-side channel 29b. The cathode 39b is for moving cations from the cation-side channel 29b to the cation removal channel 37b through the cation exchange membrane 35b.

The channel branching section 41 is for branching and introducing a liquid which has passed through the separation column 13 into the anion-side channel 29a and the cation-side channel 29b. The channel branching section 41 is, for example, configured by a frit. The connector 17 is connected to the channel branching section 41.

The frit 43a is arranged at an end portion of the anion-side channel 29a, on the opposite side from the channel branching section 41. The frit 43a is connected to the conduit 21a.

The frit 43b is arranged at an end portion of the cation-side channel 29b, on the opposite side from the channel branching section 41. The frit 43b is connected to the conduit 21b.

An ion removing liquid 47 is supplied to the anion removal channel 37a and the cation removal channel 37b. Pure water or recycled liquid waste, for example, is used as the ion removing liquid 47. A mechanism for supplying the ion removing liquid 47 is omitted from the drawing.

The eluent 27 stored in the eluent reservoir 3 is delivered through the conduit 5 by the pump 7. The outlet of the pump 7 is joined to the separation column 13 via the sample injection section 9 provided to the conduit 11. The outlet of the separation column 13 is joined to the ion processing device 19 via the conduit 15 and the connector 17. The conduit 15 is joined to the anion-side channel 29a and the cation-side channel 29b via the connector 17 and the channel branching section 41 provided inside the ion processing device 19.

The anion exchanger 33a filled in the anion-side channel 29a and the cation exchanger 33b filled in the cation-side channel 29b are separated by the bipolar membrane 31. A fluid stream which has passed through the anion-side channel 29a and the cation-side channel 29b is divided into two by the conduits 21a and 21b for each ion exchange resin layer, and the streams are detected by the conductivity detectors 23a and 23b.

At least one pair of the anode 39a and the cathode 39b is embedded in the ion processing device 19. The anode 39a and the cathode 39b are each connected to a power supply (not shown).

The anions (for example, mesyloxy group: MsO$^-$) in the eluent 27 which are introduced into the anion-side channel 29a are drawn toward the anode 39a when a voltage is applied to the anode 39a, and are led to the anion removal channel 37a through the anion exchange membrane 35a and are removed. The anions that move toward the anode 39a are, for example, F$^-$, Cl$^-$, NO$_2^-$, NO$_3^-$, PO$_4^{3-}$, SO$_4^{2-}$, Br$^-$, OH$^-$, and the like. The anions led to the anion removal channel 37a are discharged together with the ion removing liquid 47 to outside the container 45 as anion liquid waste 47a.

The cations in the eluent 27 which are introduced into the cation-side channel 29b are drawn toward the cathode 39b when a voltage is applied to the cathode 39b, and are led to the cation removal channel 37b through the cation exchange membrane 35b and are removed. The cations that move toward the cathode 39b are, for example, Na$^+$, NH$_4^+$, K$^+$, Mg$^{2+}$, Ca$^{2+}$, H$^+$, and the like. The cations led to the cation removal channel 37b are discharged together with the ion removing liquid 47 to outside the container 45 as cation liquid waste 47b.

For instance, in the case where the cations are to be detected by the non-suppressor method, the concentration of the cations (in this case, H$^+$) drawn toward the cathode 39b becomes high near the cation exchange membrane 35b, and thus, the analysis target ions, Na$^+$, are thought to become less easily removed due to Donnan effect and may be detected.

The temperature is desirably adjusted inside the oven 25 for the separation column 13 and the ion processing device 19 in order to reduce noise. Furthermore, desirably, the material of the container 45 of the ion processing device 19 is an insulating material, such as PEEK (polyetheretherketone) or acryl, from which ions are not much eluted. Also, an inert material such as PEEK is desirably used for the conduits 5, 11, 15, 21a, and 21b.

As an example, in a case where 50 µL of 1 ppm cation standard solution is injected by the sample injection section 9, the cations (for example, Na$^+$) and Cl$^-$ separated by the separation column 13 are sequentially led to the anion-side channel 29a and the cation-side channel 29b of the ion processing device 19. The counter ions (Cl$^-$) are removed through the anion exchange membrane 35a at the anion-side channel 29a.

When a voltage is applied to the cathode 39a and the anode 39b, ions of polarity opposite the applied voltage move from the interface between the anion exchange layer 31a and the cation exchange layer 31b of the bipolar membrane 31 to the anion-side channel 29a and the cation-side channel 29b. The anode reaction is $2H_2O \rightarrow O_2 + 4H^+ + 4e^-$. The cathode reaction is $2H_2O + 2e^- \rightarrow H_2 + 2OH^-$.

As an example, the stream which has become pure water due to ion removal in the anion-side channel 29a passes through the frit 43a and the conduit 21a together with the analysis target ions (Na$^+$) which has been separated, and is introduced into the first conductivity detector 21a. The analysis target ions are detected by the first conductivity detector 21a in a state where the background is low (the suppressor method, anion suppression).

On the other hand, on the side of the cation-side channel 29b, since the cation exchange membrane 35b is provided, the anions (for example, mesyloxy ion: MsO$^-$) in the eluent pass through the space of the cation exchanger 33b, and are introduced, together with the counter ions, H$^+$, into the second conductivity detector 21b via the frit 43b and the conduit 21b. The analysis target ions (Na$^+$) are detected by the second conductivity detector 21b in a state where the background is high (the non-suppressor method, anion non-suppression).

After the analysis target ions are detected, the deionized water or the recycled liquid waste is introduced into the anion removal channel 37a and the cation removal channel 37b as the ion removing liquid 47. In the present example, the ion removing liquid 47 is introduced into the anion removal channel 37a and the cation removal channel 37b in the forward direction (the same direction as the flow of the eluent), but it may alternatively be introduced in the backward direction.

Heretofore, analysis of cations has been described, but analysis may be performed simultaneously in the same manner for the anions by the suppressor method and the non-suppressor method by using the ion chromatograph 1 of the example described above. At the time of analysis of anions, cations are moved from the cation-side channel 29b to the cation removal channel 37b through the cation exchange membrane 35b and are removed, and the analysis target anions are detected by the second conductivity detector 23b by the suppressor method (cation suppression). Further, since the cations are not removed in the anion-side channel 29a, the analysis target anions may be detected by the first conductivity detector 23a by the non-suppressor method (cation non-suppression).

Figure 2:
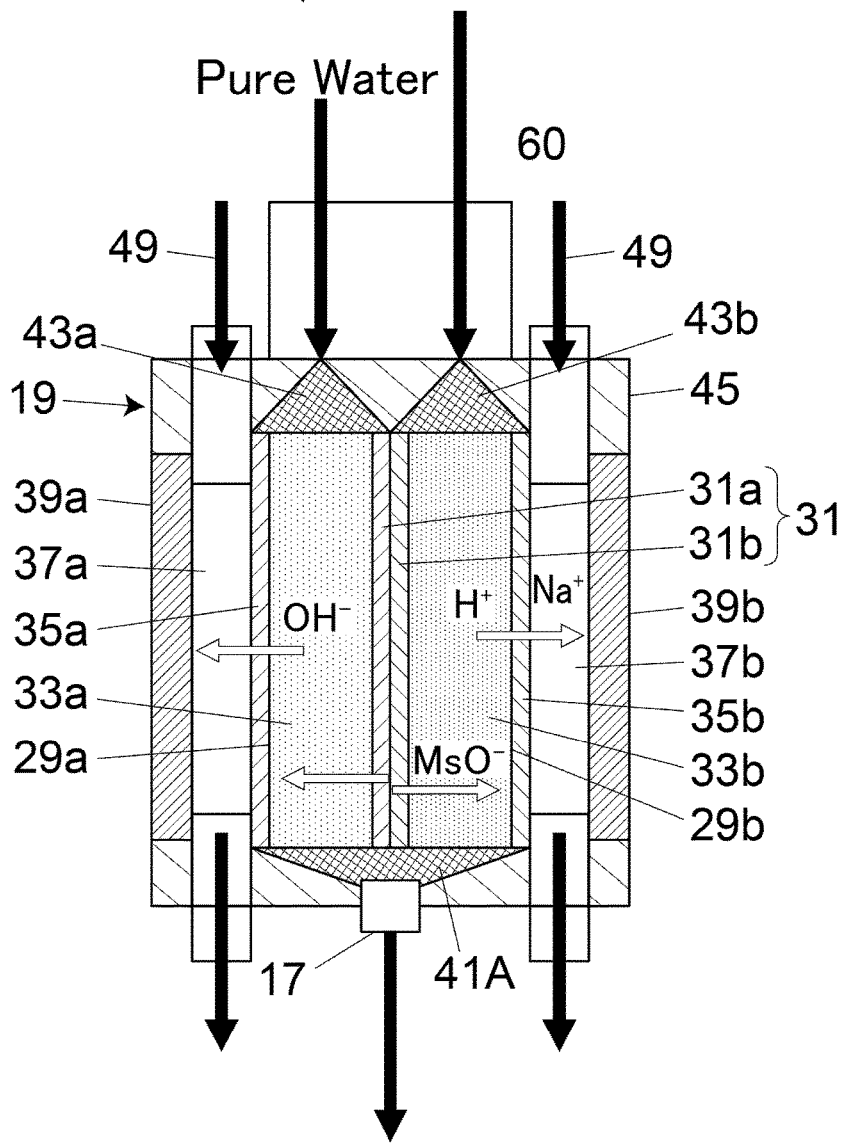
FIG. 2 is a schematic configuration diagram for describing an example of an eluent generator.
Figure 3:
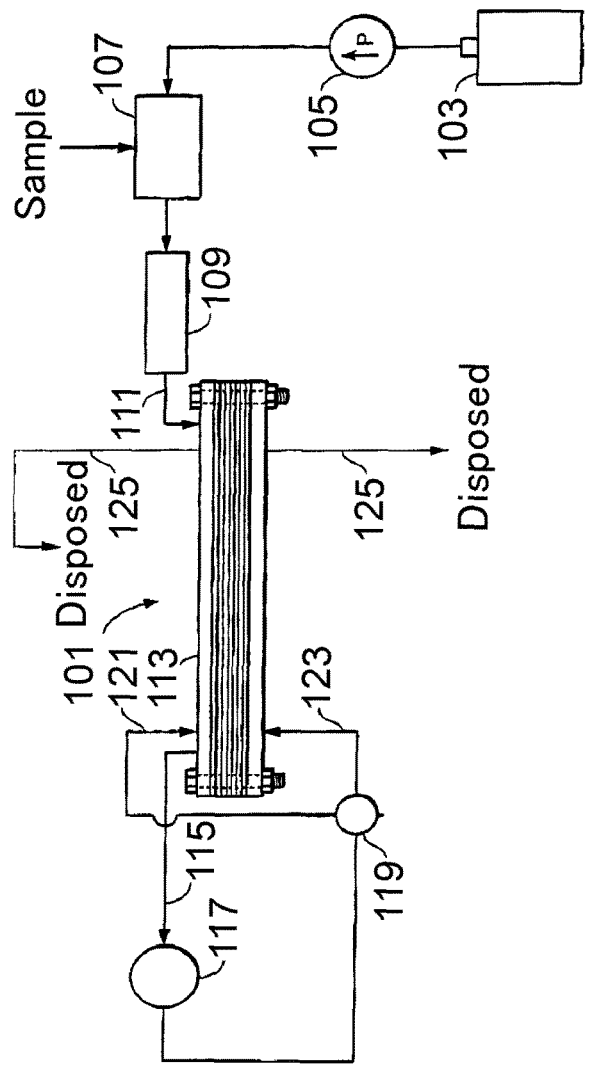
FIG. 3 is a schematic configuration diagram for describing a conventional ion chromatograph provided with an electrodialysis suppressor.

FIG. 2 is a schematic configuration diagram of the ion processing device for describing an example of an eluent generator. The configuration of the ion processing device is the same as that shown in FIG. 1. When an electrolyte solution is to be generated using the ion processing device 19, the inlet and the outlet of the stream are reversed from when the ion processing device 19 is applied to the ion chromatograph. As a concentrated electrolyte solution, a 50 mM sodium methanesulfonate (MSANa) solution is used, for example. The basic configuration of the ion processing device 19 is the same as that shown in FIG. 1, and thus, description of each part of the ion processing device 19 is omitted.

The present inventor has found that, by using the ion processing device 19 and by reversing the inlets and the outlets of the anion-side channel 29a and the cation-side channel 29b for the streams from when the ion processing device 19 is applied to the ion chromatograph, Na$^+$ may be removed from the electrolyte solution (MSANa) by electrical means to generate acid, and then, by further mixing water, an electrolyte solution, for example, to be used as an eluent may be generated.

Pure water is introduced into the anion-side channel 29a from the frit 43a side, as an example. Further, the electrolyte solution (MSANa) is introduced into the cation-side channel 29b from the frit 43b side. The part for supplying liquids to the frits 43a and 43b is a solution supply section 60.

A liquid which has passed through the anion-side channel 29a and a liquid which has passed through the cation-side channel 29b are mixed at a channel merging section 41A, and are discharged from the connector 17.

An ion removing liquid 49 is introduced into the anion removal channel 37a and the cation removal channel 37b. As the ion removing liquid 49, pure water or recycled liquid waste, for example, are used. Additionally, the streaming direction of the ion removing liquid 49 in the anion removal channel 37a and the cation removal channel 37b is not particularly specified.

A voltage of about 3 to 10 V is applied by the electrical means by using, for example, a DC power supply. The concentration of an acid to be generated may be controlled by the amount of electricity by Faraday's law. Further, the electrolyte solution is not limited to that illustrated as long as it includes an acid.

Generation of an electrolyte solution which may be used as an eluent for cation analysis has been described above, but an electrolyte solution which may be used as an eluent for anion analysis may also be generated in the same manner by using the ion processing device 19.

As an example, an electrolyte solution which may be used as an eluent for anion analysis may be generated simply by introducing an electrolyte solution (for example, sodium hydrogen sulfate) into the anion-side channel 29a from the frit 43a side, and introducing pure water into the cation-side channel 29b from the frit 43b side.

Heretofore, an example of the present invention has been described, but the configuration, arrangement, numerical values, materials, and the like in the example are only exemplary, and the present invention is not limited to those described above. Various modifications may be made within the scope of the present invention described in the claims.

For instance, in the example described above, an ion exchange resin is used as the ion exchanger, but the ion exchanger of the present invention is not limited to the ion exchange resin. In the present invention, the ion exchanger may be any substance having an ion exchange action.

Further, in the example described above, a frit is used as the channel branching section 41, but the channel branching section of the present invention is not limited to a frit. In the present invention, the channel branching section is not particularly limited as long as a liquid to be introduced into the anion-side channel and the cation-side channel may be branched and introduced into the anion-side channel and the cation-side channel.

Furthermore, in the example described above, the ion processing device 19 is provided with the channel branching section 41, but the ion processing device of the present invention does not have to be provided with the channel branching section. In the present invention, a liquid which has passed through the separation column may be branched outside the ion processing device of the present invention, and may be introduced into the anion-side channel and the cation-side channel.

Moreover, in the example described above, anions or cations are simultaneously detected by both the non-suppressor method and the suppressor method based on the detection signals of both the first conductivity detector and the second conductivity detector, but the present invention is not limited to such an example. In the present invention, anions or cations may be detected by the non-suppressor method or the suppressor method based on the detection signal of one of the first conductivity detector and the second conductivity detector.

The ion processing device of the present invention may be used as a device which is, at the time of analysis of anions or cations in the field of ion chromatography, capable of suppressing the backgrounds of the eluents for both the anions and the cations by one device.

Furthermore, the ion processing device of the present invention may be used as a device which is capable of generating both an eluent for anion analysis and an eluent for cation analysis.

What is claimed is:

1. An ion processing device comprising:
   a bipolar membrane that is formed by stacking an anion exchange layer and a cation exchange layer;
   an anion-side channel that is arranged in contact with the anion exchange layer of the bipolar membrane, and that is filled with an anion exchanger;
   an anion removal channel that is arranged in contact with the anion-side channel via an anion exchange membrane;
   an anode configured to move anions from the anion-side channel to the anion removal channel through the anion exchange membrane;
   a cation-side channel that is arranged in contact with the cation exchange layer of the bipolar membrane, and that is filled with a cation exchanger;
   a cation removal channel that is arranged in contact with the cation-side channel via a cation exchange membrane,
   a cathode configured to move cations from the cation-side channel to the cation removal channel through the cation exchange membrane; and
   a channel branching section configured to divide and introduce a liquid from one channel into the anion-side channel and the cation-side channel.

2. An ion chromatograph comprising:
   a separation column configured to separate a sample;
   an eluent delivery section configured to deliver an eluent to the separation column;
   a sample injection section configured to inject a sample into a flow of the eluent that is delivered by the eluent delivery section to the separation column;
   a suppressor that is connected to an eluent outlet side of the separation column, the suppressor being an ion processing device including
   a bipolar membrane that is formed by stacking an anion exchange layer and a cation exchange layer,
      an anion-side channel that is arranged in contact with the anion exchange layer of the bipolar membrane, and that is filled with an anion exchanger,
      an anion removal channel that is arranged in contact with the anion-side channel via an anion exchange membrane,
      an anode configured to move anions from the anion-side channel to the anion removal channel through the anion exchange membrane,
      a cation-side channel that is arranged in contact with the cation exchange layer of the bipolar membrane, and that is filled with a cation exchanger,
      a cation removal channel that is arranged in contact with the cation-side channel via a cation exchange membrane, and
      a cathode configured to move cations from the cation-side channel to the cation removal channel through the cation exchange membrane, and
      a channel branching section configured to divide and introduce the eluent flowing out of the separation column into the anion-side channel and the cation-side channel;
   a first conductivity detector that is, with respect to the suppressor, connected to the anion-side channel on an opposite side from the channel branching section; and a second conductivity detector that is, with respect to the ion processing device, connected to the cation-side channel on the opposite side from the channel branching section.

3. The ion chromatograph according to claim 2, further comprising a data processing section that is connected to the first conductivity detector and the second conductivity detector,
  wherein the data processing section is configured to simultaneously detect anions or cations by both a non-suppressor method and a suppressor method based on detection signals of both the first conductivity detector and the second conductivity detector.

\* \* \* \* \*